United States Patent
Lu et al.

(10) Patent No.: US 10,576,452 B2
(45) Date of Patent: Mar. 3, 2020

(54) METHOD AND DEVICE FOR MAKING POLYMER MICROPARTICLES

(71) Applicant: GENERAL ELECTRIC COMPANY, Schenectady, NY (US)

(72) Inventors: Lianghua Lu, Shanghai (CN); Lin Chen, Shanghai (CN); Jie Gao, Shanghai (CN); Zhida Pan, Shanghai (CN); Wenqing Peng, Shanghai (CN); Tobias E. Soderman, Uppsala (SE)

(73) Assignee: General Electric Company, Schenectady, NY (US)

( * ) Notice: Subject to any disclaimer, the term of this patent is extended or adjusted under 35 U.S.C. 154(b) by 235 days.

(21) Appl. No.: 15/564,265

(22) PCT Filed: Mar. 1, 2016

(86) PCT No.: PCT/EP2016/054280
§ 371 (c)(1),
(2) Date: Oct. 4, 2017

(87) PCT Pub. No.: WO2016/162143
PCT Pub. Date: Oct. 13, 2016

(65) Prior Publication Data
US 2018/0133685 A1    May 17, 2018

(30) Foreign Application Priority Data
Apr. 8, 2015    (CN) .......................... 2015 1 0163884

(51) Int. Cl.
*B01J 2/06*    (2006.01)
*B01J 2/08*    (2006.01)
(Continued)

(52) U.S. Cl.
CPC ............... *B01J 20/24* (2013.01); *B01J 2/04* (2013.01); *B01J 2/06* (2013.01); *B01J 2/08* (2013.01);
(Continued)

(58) Field of Classification Search
None
See application file for complete search history.

(56) References Cited

U.S. PATENT DOCUMENTS

| 5,147,895 A | 9/1992 | Hughes et al. |
| 5,223,550 A | 6/1993 | Hughes et al. |

(Continued)

FOREIGN PATENT DOCUMENTS

| WO | 93/12178 A1 | 6/1993 |
| WO | 01/30146 A1 | 5/2001 |
| WO | 02/12374 A1 | 2/2002 |

OTHER PUBLICATIONS

Schlick Solutions, Module System Range 0/2-0/9, product brochure, pp. 60-71, no date, available at myschlick.com on Jul. 29, 2019.*

(Continued)

*Primary Examiner* — Mary Lynn F Theisen
(74) *Attorney, Agent, or Firm* — Eversheds Sutherland (US) LLP

(57) ABSTRACT

A method includes spraying a liquid including polymer and a gas substantially inert to the liquid respectively from a first and second orifice of a nozzle into air to form mist of beads. The beads then are collected with a collecting medium at a temperature in a range from about −10° C. to about 80° C. The collecting medium includes at least one of water and alcohols.

30 Claims, 6 Drawing Sheets

(51) Int. Cl.
- *B01J 2/04* (2006.01)
- *B01J 20/24* (2006.01)
- *B01J 13/00* (2006.01)
- *B01J 20/26* (2006.01)
- *B01J 20/28* (2006.01)
- *B01J 20/285* (2006.01)
- *B01J 20/286* (2006.01)
- *B01J 4/00* (2006.01)
- *B01J 20/281* (2006.01)
- *B01J 20/30* (2006.01)
- *C07K 1/16* (2006.01)
- *C07K 1/18* (2006.01)
- *C07K 1/22* (2006.01)

(52) U.S. Cl.
CPC .............. *B01J 4/002* (2013.01); *B01J 13/00* (2013.01); *B01J 20/262* (2013.01); *B01J 20/267* (2013.01); *B01J 20/281* (2013.01); *B01J 20/28004* (2013.01); *B01J 20/285* (2013.01); *B01J 20/286* (2013.01); *B01J 20/28016* (2013.01); *B01J 20/28019* (2013.01); *B01J 20/3007* (2013.01); *B01J 20/3085* (2013.01); *C07K 1/16* (2013.01); *C07K 1/18* (2013.01); *C07K 1/22* (2013.01); *B01J 2220/52* (2013.01)

(56) References Cited

U.S. PATENT DOCUMENTS

| | | | | |
|---|---|---|---|---|
| 5,662,840 A * | 9/1997 | Thomas | ............ | B01J 13/00 264/12 |
| 6,248,268 B1 * | 6/2001 | Cook | ............ | C08J 3/122 210/656 |
| 6,602,990 B1 * | 8/2003 | Berg | ............ | B01J 20/262 536/124 |
| 6,841,097 B2 * | 1/2005 | Andersson | ............ | B01J 2/08 264/5 |
| 7,341,682 B2 * | 3/2008 | Andersson | ............ | B01J 20/26 264/5 |
| 7,396,467 B2 * | 7/2008 | Berg | ............ | B01J 20/24 210/198.2 |
| 8,372,286 B2 * | 2/2013 | Glad | ............ | B01J 20/262 210/198.2 |
| 8,545,739 B2 * | 10/2013 | Cocchietto | ............ | A61K 9/1652 264/13 |
| 2002/0164364 A1 * | 11/2002 | Quong | ............ | A01N 25/26 424/417 |
| 2011/0250264 A1 | 10/2011 | Schutt et al. | | |

OTHER PUBLICATIONS

PCT International Search Report and Written Opinion for PCT Application No. PCT/EP2016/054280 dated May 31, 2016 (14 pages).

* cited by examiner a)

b)

METHOD AND DEVICE FOR MAKING POLYMER MICROPARTICLES

CROSS REFERENCE TO RELATED APPLICATIONS

This application claims the priority benefit of PCT/EP2016/054280 filed on Mar. 1, 2016 which claims priority benefit of Chinese Application No. 201510163884.7 filed Apr. 8, 2015. The entire contents of which are hereby incorporated by reference herein.

BACKGROUND

A critical step in biomolecular drug manufacture is the separation of "proteins of interest", the active elements in drugs, from other materials. This separation step is mostly based on chromatography technology with suitable separation media. The most widely used separation media in chromatography is polymer microparticles such as polysaccharide beads.

Polysaccharide beads are traditionally produced by emulsion processes, in which an aqueous solution of the polysaccharide is poured into a hydrophobic solvent in a stirring vessel. As the polysaccharide solution and the hydrophobic solvent are immiscible with each other, agitation turns the two liquids into an emulsion with the polysaccharide solution as droplets suspended in the hydrophobic solvent. A water-in-oil emulsifier soluble in the hydrophobic solvent may be added to stabilize the droplets so they do not coalesce into larger ones. The emulsion is then cooled to cause the droplets to gel to form microparticles of the polysaccharide. As the emulsion processes involve use of large amount of environmentally unfriendly solvents such as toluene, intensive washing is needed to remove the solvents in the polysaccharide microparticles in order to meet the downstream application requirement.

As the industry is facing more and more stringent environmental requirements, there is a need for a more environmentally friendly process of making microparticles.

BRIEF DESCRIPTION

In one aspect, a method includes spraying a liquid including polymer and a gas substantially inert to the liquid respectively from a first and second orifice of a nozzle into air to form a mist of beads. The beads are then collected with a collecting medium at a temperature in a range from about −10° C. to about 80° C. The collecting medium includes at least one of water and alcohols.

In another aspect, a system includes a nozzle configured to spray a liquid including polymer and a gas substantially inert to the liquid from a first and second orifice thereof, respectively, to form a mist of beads, and a receiving unit containing a collecting medium for collecting the beads. The collecting medium includes at least one of water and alcohols. The system further includes a liquid feeding device configured to feed the liquid into the first orifice of the nozzle and a gas feeding device configured to feed the gas to the second orifice of the nozzle.

BRIEF DESCRIPTION OF THE DRAWINGS

The above and other aspects, features, and advantages of the present disclosure will become more apparent in light of the subsequent detailed description when taken in conjunction with the accompanying drawing in which.

DETAILED DESCRIPTION

One or more embodiments of the present disclosure will be described below. Unless defined otherwise, technical and scientific terms used herein have the same meaning as is commonly understood by one of ordinary skill in the art to which this invention belongs. The terms "a" and "an" do not denote a limitation of quantity, but rather denote the presence of at least one of the referenced items. The term "or" is meant to be inclusive and mean any, some, or all of the listed items. The use of "including," "comprising" or "having" and variations thereof herein are meant to encompass the items listed thereafter and equivalents thereof as well as additional items.

Approximating language, as used herein throughout the specification and claims, may be applied to modify any quantitative representation that could permissibly vary without resulting in a change in the basic function to which it is related. Accordingly, a value modified by a term or terms, such as "about" and "substantially", are not to be limited to the precise value specified. Additionally, when using an expression of "about a first value–a second value," the about is intended to modify both values. In at least some instances, the approximating language may correspond to the precision of an instrument for measuring the value. Here, and throughout the specification and claims, range limitations may be combined and/or interchanged, such ranges are identified and include all the sub-ranges contained therein unless context or language indicates otherwise.

Embodiments of the present disclosure refer to an environmentally-friendly method and system for producing polymer microparticles, in which a two-phase spray nozzle is used to spray a polymer-containing liquid and a gas substantially inert to the liquid respectively from a first and second orifice thereof into air to form a mist of beads, followed by collecting the beads with a collecting medium including at least one of water and alcohols. As the collecting medium without harmful solvent is used, such a method and system is environmentally-friendly. Moreover, intensive washing steps for removing solvent are no longer necessary, which simplifies the process and reduces the cost. Furthermore, a narrow particle size distribution can be achieved through such a method and system, by fine-tuning the system parameters.

Figure 1:
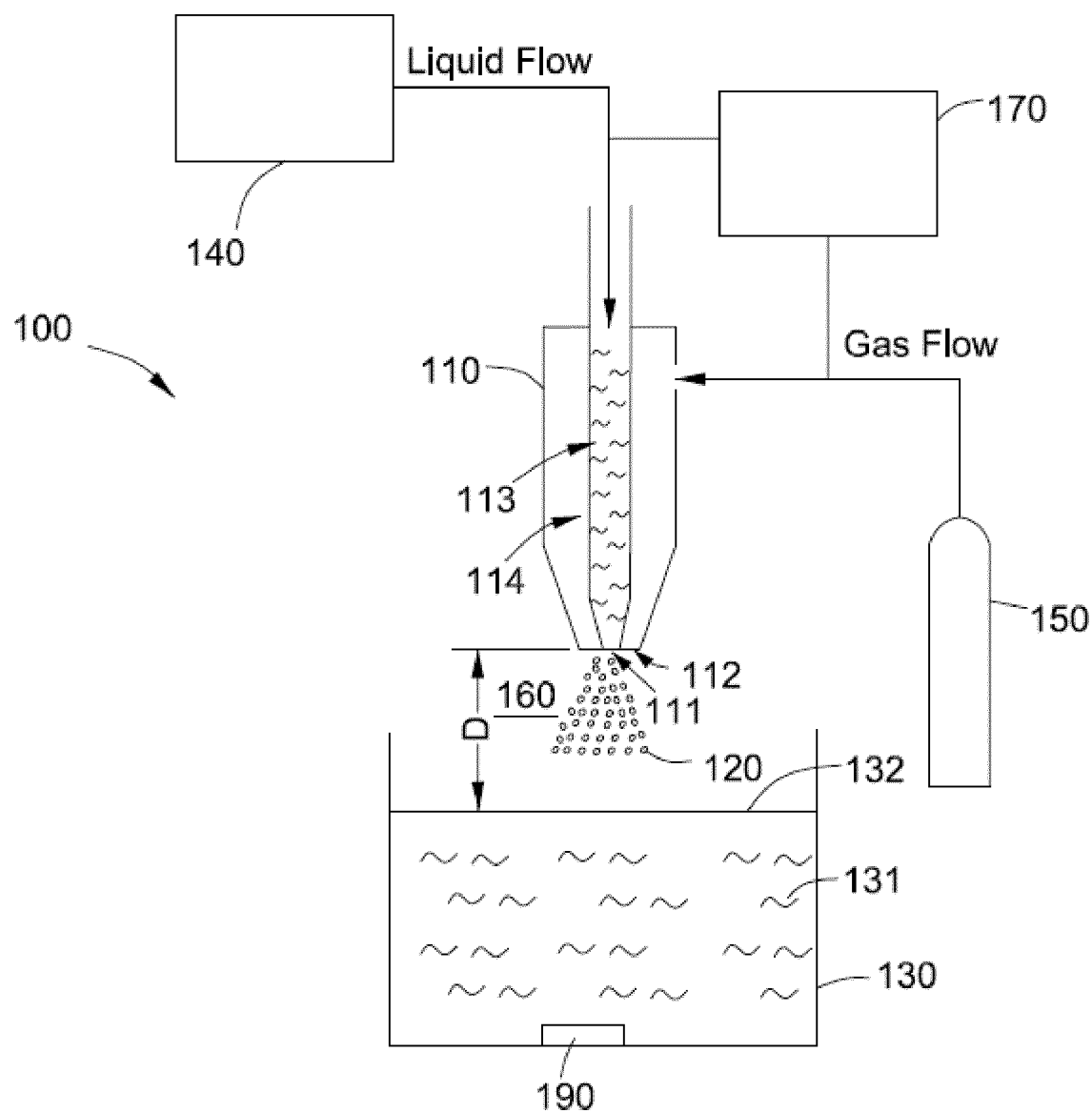
FIG. 1 is a schematic diagram illustrating an exemplary system for producing polymer microparticles with an external mix two-phase spray nozzle, according to one embodiment of the present disclosure.

Referring to FIG. 1, an exemplary system 100 for producing microparticles of a polymer such as a polysaccharide is illustrated. The system 100 includes a two-phase spray nozzle 110, which has a first and second orifice 111 and 112 and is configured to spray a liquid including the polymer and a gas substantially inert to the liquid from the first and second orifices 111 and 112, respectively. The liquid and gas sprayed respectively from the first and second orifices 111 and 112 are caused to interact with each other so as to atomize the liquid to form mist of beads 120. The system 100 further includes a receiving unit 130 containing a collecting medium 131 for collecting the mist of beads 120. The collecting medium 131 includes at least one of water and alcohols, and it may be, for example, water, an alcohol, combinations of water and an alcohol, combinations of different alcohols, or combinations of water and alcohols. Various environmentally green alcohols can be used. Examples of the applicable alcohols include but are not limited to methanol, ethanol, propanol, isopropanol, n-butanol and combinations thereof. The collecting medium can e.g. be water or an aqueous solution comprising at least 90 wt % water. The solution may further comprise 0-10 wt %, such as 0.01-5 wt %, of a wetting agent, which can e.g. be a surfactant and/or one or more of the alcohols mentioned above. An advantage of using water or an aqueous solution as described above is that open handling of flammable liquids is avoided. A liquid feeding device 140 is configured to feed the liquid into the first orifice 111 of the nozzle 110. A gas feeding device 150 is configured to feed the gas to the second orifice 112 of the nozzle 110.

The first and second orifices 111, 112 of the nozzle 110 are spaced from a collecting surface 132 of the collecting medium 131 in the receiving unit 130, and thus there is an air interval 160 (a distance D) between the first and second orifices 111, 112 and the collecting surface 132. The interaction of the liquid and the gas and atomization of the liquid occur in the air interval 160. In some embodiments, the air interval 160 is configured to allow at least a part of the beads to be solidified into microparticles before the beads enter the collecting medium 131. In some specific embodiments, the first and second orifices 111, 112 are no less than about 2 centimeters, or preferably no less than about 5 centimeters, or more preferably no less than about 10 centimeters from the collecting surface 132, depending on the scale of the system 100. In particular, the first and second orifices 111, 112 may be no less than about 25 centimeters from the collecting surface 132. The air interval distance D can e.g. be at least 30 cm, such as at least 70 cm or at least 100 cm or 100-150 cm, particularly for the production of beads in the 30-100 micrometer diameter range. The environment in the air interval 160 may be controlled with respect to temperature and relative humidity to control solidification of the mist into microparticles and, if needed, to avoid evaporation effects which may affect the porosity of the microparticles. In particular, the relative humidity in the air interval may be controlled to be at least 90%, such as at least 95% or 95.0-99.9%. The temperature in the air interval may be a gradient from a nozzle temperature at the first and second orifices 111,112 to a collecting medium temperature at the collecting surface 132. This temperature gradient can be smooth and it can e.g. be linear or non-linear. Technical solutions for controlling such an environment by closed containment and/or injection of steam are described in e.g. U.S. Pat. Nos. 6,841,097, 7,207,499 and WO2014148966A1, which are hereby incorporated by reference in their entireties. Further, the liquid may contain a humectant, such as a glycol, to limit any evaporation rate, e.g. as described in U.S. Pat. No. 7,341,682, which is hereby incorporated by reference in its entirety. The liquid may also contain other additives such as salts, buffers etc.

Figure 2:
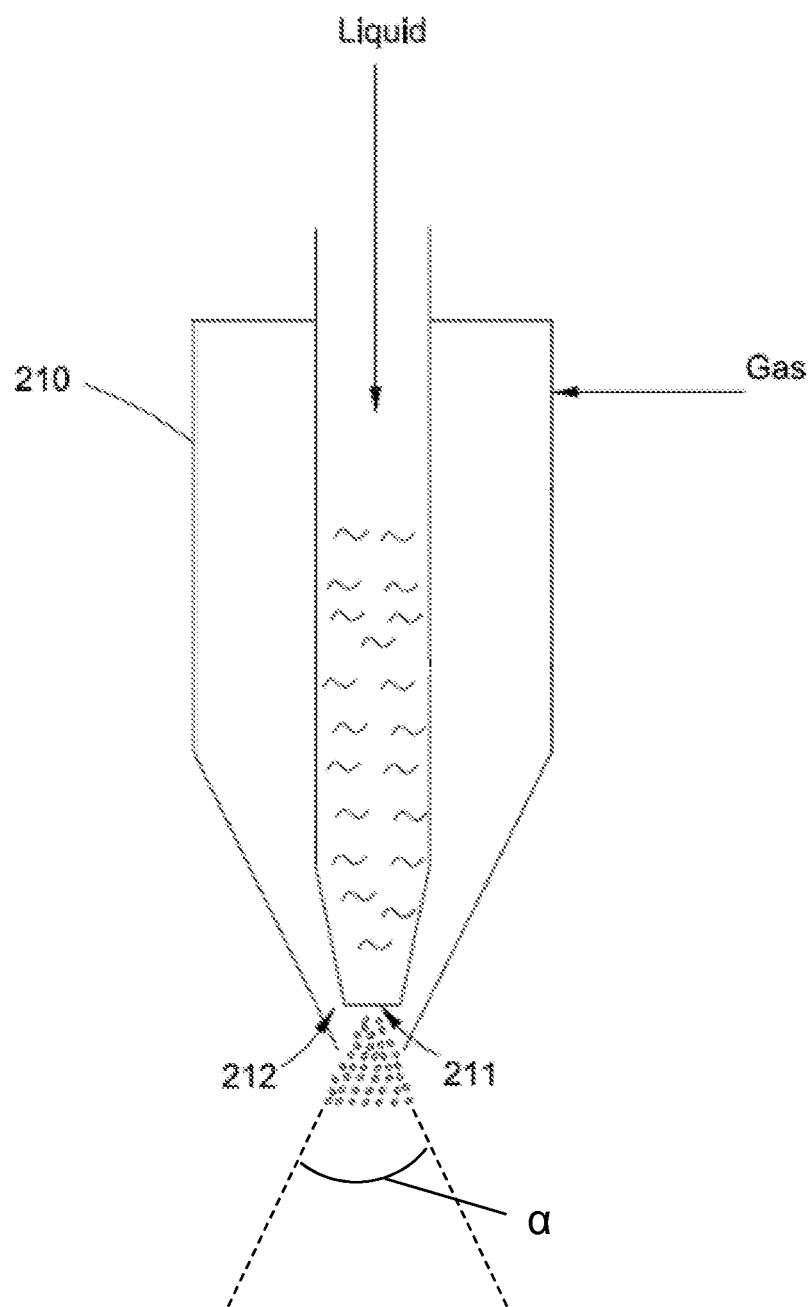
FIG. 2 is a schematic diagram illustrating an exemplary internal mix two-phase spray nozzle.

As used herein, the term "two-phase spray nozzle", which is sometimes called "two-fluid spray nozzle", refers to a nozzle that causes interaction of a liquid and a gas to atomize the liquid. Depending on the mixing point of the liquid and gas streams relative to the nozzle face, two-phase spray nozzles are grouped into internal mix nozzles and external mix nozzles, both of which are applicable to the systems described herein. The nozzle 110 as illustrated in FIG. 1 is an external mix nozzle wherein the interaction of the liquid and the gas occurs at a mixing point outside the nozzle 110. The liquid and the gas respectively fed to the first and second orifices 111, 112 do not interact with each other before they exit the nozzle 110. However, the external mix nozzle 110 may be replaced with an internal mix nozzle in alternative embodiments. FIG. 2 illustrates an exemplary internal mix nozzle 210 wherein the interaction of the liquid and the gas occurs at a mixing point inside the nozzle 210. Liquid and gas respectively fed to a first orifice 211 and a second orifice 212 of the nozzle 210 interact with each other to atomize the liquid before they exit the nozzle 210. Comparing with the external mix nozzle, the internal mix nozzle may offer better environment for atomization because the environment at mixing point inside the internal mix nozzle is more controllable, which may benefit micronization of the liquid.

The nozzles 110 and 210 have substantially the same configuration except the location of the mixing point relative to the nozzle face. The configuration of the nozzle 110 will be described in detail hereinafter as an example. The nozzle 110 includes a first channel 113 in fluid communication with the first orifice 111, which allows the liquid fed from the liquid feeding device 140 to flow to the first orifice 111, and a second channel 114 in fluid communication with the second orifice 112, which allows the gas fed from the gas feeding device 150 to flow to the second orifice 112. In the illustrated embodiment, the second channel 114 is an annular channel surrounding the first channel 113, and the second orifice 112 is an annular opening surrounding the first orifice 111.

The foregoing nozzles 110 and 210 should be considered as illustrative rather than limiting on the configuration of the nozzle. There are many other configurations as for either external mix nozzle or internal mix nozzle, and nozzles of various configurations are applicable to the systems of the present disclosure if only they are capable of causing interaction of a liquid and a gas to atomize the liquid. Nozzles producing many different spray patterns are available. For the present purpose, a substantially conical spray pattern with a spray angle α (as illustrated in FIG. 2) may be advantageous. The spray angle may e.g. be less than 90 degrees, such as less than 45 degrees or less than 20 degrees, which is advantageous particularly for the production of beads in the 30-100 micrometer diameter range.

Figure 3:
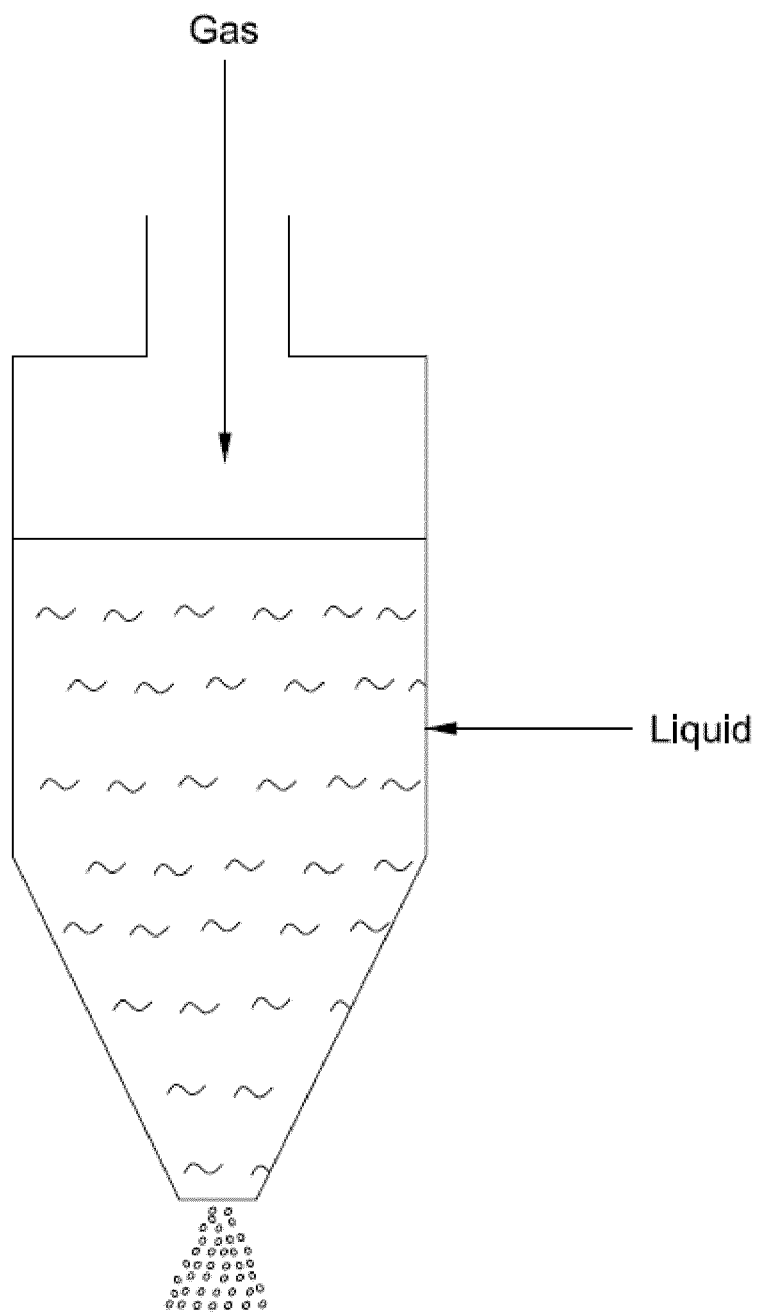
FIG. 3 is a schematic diagram illustrating a single-fluid or hydraulic spray nozzle.

The two-phase spray nozzle enables the liquid and gas to be independently fed and sprayed, and thus the sizes of the beads can be adjusted and controlled by adjusting feeding conditions of at least one of the liquid and gas. For example, the sizes of the beads may be controlled by adjusting the flow rate ratio between the liquid and the gas. Comparing with a single-fluid or hydraulic spray nozzle as illustrated in FIG. 3, which utilizes kinetic energy of a liquid to break it up into droplets, the two-phase spray nozzle offers significant advantages on controlling the sizes of the beads, which makes the sizes of the beads more controllable. Therefore, beads of smaller sizes can be obtained and the sizes of the beads can be more precisely controlled with the systems described herein. Moreover, the liquid and gas can be fed at lower pressures with the two-phase spray nozzle.

The system 100 may further include a control device 170 configured to adjust and control conditions for feeding the liquid and gas into the nozzle 110 and thereby enable the liquid and gas to be fed into the nozzle 110 under different conditions. The adjustable conditions include but are not limited to pressures, temperatures, flow rates, or combinations thereof. In an example, the control device 170 enables a mass flow rate ratio between the liquid and the gas adjustable in a predetermined range, for example, from about 0.1 to about 10.

The system 100 may further include at least one of heating devices and thermo-insulation devices (not shown) thermally coupled to at least one of the liquid feeding device 140 and the nozzle 110. In some embodiments, the liquid feeding device 140 is coupled with a heat-jacket for keeping the temperature of the feeding liquid. In some embodiments, the nozzle 110 is coupled with a heat jacket for keeping the temperature of the liquid and gas in the nozzle 110. Moreover, the system 100 may further include a dispersing device 190 configured to cause the collecting medium 131 to move or disperse in the receiving unit 130. The dispersing device 190 may be any device that is configured to stir the collecting medium 131 or cause the collecting medium 131 to bubble or flow or move in other manners. Examples of the dispersing device 190 include but are not limited to stirrers for stirring the collecting medium 131, devices for causing the collecting medium 131 to bubble in the receiving unit 130, pumps for causing the collecting medium 131 to flow, and combinations thereof.

In use, a liquid containing polymer, for example, an aqueous solution of the polymer, and a gas substantially inert to the liquid are respectively injected into the first and second channels 113 and 114, and then respectively sprayed from the first and second orifices 111 and 112 into the air interval 160 to form a mist of beads. The beads are collected with the collecting medium 131 in the receiving unit 130, which may be maintained at a temperature in a range from about −10° C. to about 80° C., or preferably in a range from about 0° C. to about 50° C. The beads may be cooled in the air interval 160, and in some embodiments, further cooled in the collecting medium 131 to form solid microparticles. In some embodiments, microparticles of a particle size in a range from about 20 micrometers to about 500 micrometers can be obtained. These beads and microparticles have a roundness and strength sufficient to preserve the structural integrity upon collection thereof, even when the collecting medium 131 includes water or alcohols that are not hydrophobic.

The liquid fed to the first orifice 111 may be driven, for example, by pumping, siphoning, by hydraulic power, or by a pressurised gas that may be the same as or different from the gas fed into the second orifice 112. The gas fed to the second orifice 112 may be air, nitrogen, argon or other inert gases. The liquid and gas may be fed into the nozzle 110 under different conditions including pressures, temperatures, flow rates, or combinations thereof. In some embodiments, the liquid is injected into the first channel 113 of the nozzle 110 at a temperature in a range from about 65° C. to about 100° C., or preferably in a range from about 75° C. to about 85° C. In some embodiments, the gas is injected into the second channel 114 of the nozzle 110 at a temperature in a range from about 0° C. to about 60° C., or preferably in a range from about 20° C. to about 50° C. In some embodiments, a mass flow rate ratio between the liquid and the gas is controlled in a desired range, for example, from about 0.1 to about 10, to obtain polymer microparticles with good particle size distribution. In some embodiments, the collecting medium 131 in the receiving unit 130 is stirred or caused to flow in order to prevent aggregation.

The systems and methods of the present disclosure are applicable to a wide range of polymer, and are particularly applicable to polysaccharides including but not limited to native or derivatised agarose, agar, carrageenan, konjac glucomannan, dextran, cellulose, chitosan, starch, and combinations thereof. Thermally gelating polysaccharides like agarose, agar and carrageenan are particularly suitable. A non-limiting example of producing agarose microparticles will be described hereinafter to demonstrate the methods of the present disclosure.

The microparticles may be further processed to improve their usability in e.g. chromatographic separation processes. Polysaccharide microparticles can suitably be crosslinked in a subsequent step to stabilize them and to increase their rigidity. Crosslinking reagents such as e.g. epichlorohydrin, diepoxides, allyl glycidyl ether or divinylsulfone may be used, as exemplified by U.S. Pat. Nos. 3,507,851, 4,665,164, 4,973,683 and 3,959,251, which are hereby incorporated by reference in their entireties. Particularly high rigidities may be achieved by crosslinking derivatised polysaccharides, as described in U.S. Pat. Nos. 6,602,990 or 7,396,467, which are hereby incorporated by reference in their entireties.

Also, the microparticles may be derivatised with ligands for binding target molecules in e.g. chromatographic separations. The ligands can be e.g. cation exchange ligands (e.g. ligands comprising sulfopropyl, sulfoethyl or carboxymethyl groups), anion exchange ligands, (e.g. comprising trimethylammonium or diethylaminoethyl groups), hydrophobic ligands (e.g. comprising butyl, hexyl, octyl or phenyl groups) or multimodal groups (e.g. comprising cation or anion exchange groups in combination with hydrophobic groups). The ligands can also be affinity ligands for binding to specific protein types. Commonly used examples of affinity ligands include Protein A, Protein G, Protein L, antibodies, lectins, streptavidin etc.

EXAMPLE

In this example, agarose powder (from BioWest Co., Ltd., Spain) was used as the material for preparing the agarose solution. Ethanol (from SinoPharm Group Co., Ltd., China) was used as the collecting medium. A dispenser (Biodot AirJet Quanti 3000, from BioDot Co., Ltd., USA) was used as the two-phase spray nozzle to atomize the agarose solution to generate the mist of beads. A peristaltic pump (from Baoding Longer Precision Pump Co., Ltd., China) was used as the liquid feeding device for feeding the agarose solution into the first orifice of the nozzle. An airflow controller with the scale of 10 L/min (CS 100, from SevenStar Co., Ltd., China) was used as the gas feeding device for feeding the gas to the second orifice of the nozzle.

400 ml of 4% by weight agarose solution was prepared by adding 16 g of the agarose powder to 384 mL water. The agarose solution was heated with a microwave oven for about 5 minutes to generate a homogeneous solution. Then the homogeneous agarose solution was poured into a beaker of about 250 mL, which was disposed in a water bath of about 90° C. The homogeneous agarose solution was transferred with the peristaltic pump from the beaker to the nozzle at a flow rate of about 3 mL/min and kept at a temperature in a range from about 75° C. to about 85° C. A stream of air was fed into the nozzle at a flow rate of about 4.3 L/min. The droplets of the agarose solution generated through the nozzle were collected and cooled by a container with 800 mL of 95% by volume ethanol solution at about 4°

C. with stirring at 200-300 rpm. The agarose beads formed in the container were collected and concentrated by a centrifuge and stored at a fridge for following estimation or investigation.

Figure 4:
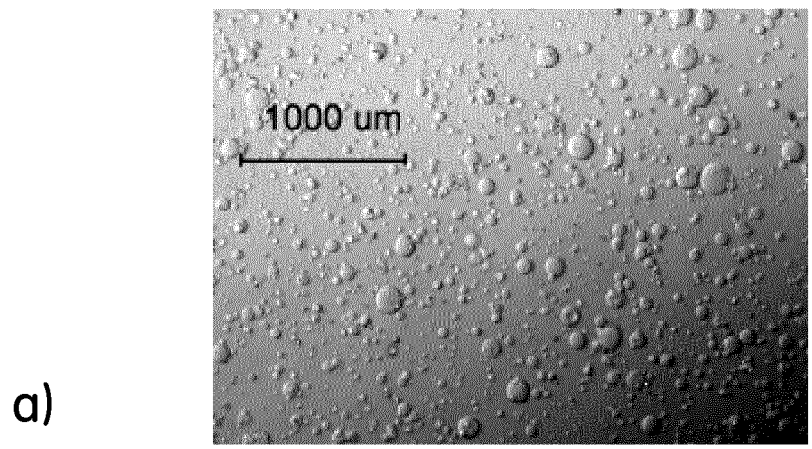
FIGS. 4A and 4B illustrate particle images of an agarose bead sample obtained in an example of the present disclosure, observed by microscopy with two different magnifications, respectively.
Figure 4:
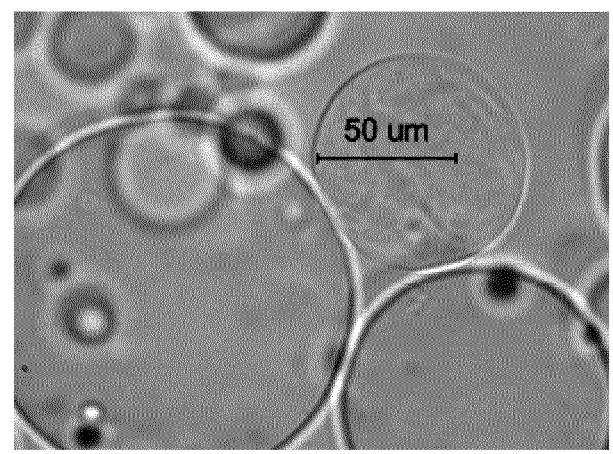

Particle roundness of the agarose beads was estimated by microscopy. FIGS. 4A and 4B illustrate the agarose beads observed by microscopy with 20× and 400× magnifications, respectively. It can be seen that the agarose beads have very good particle roundness.

Figure 5:
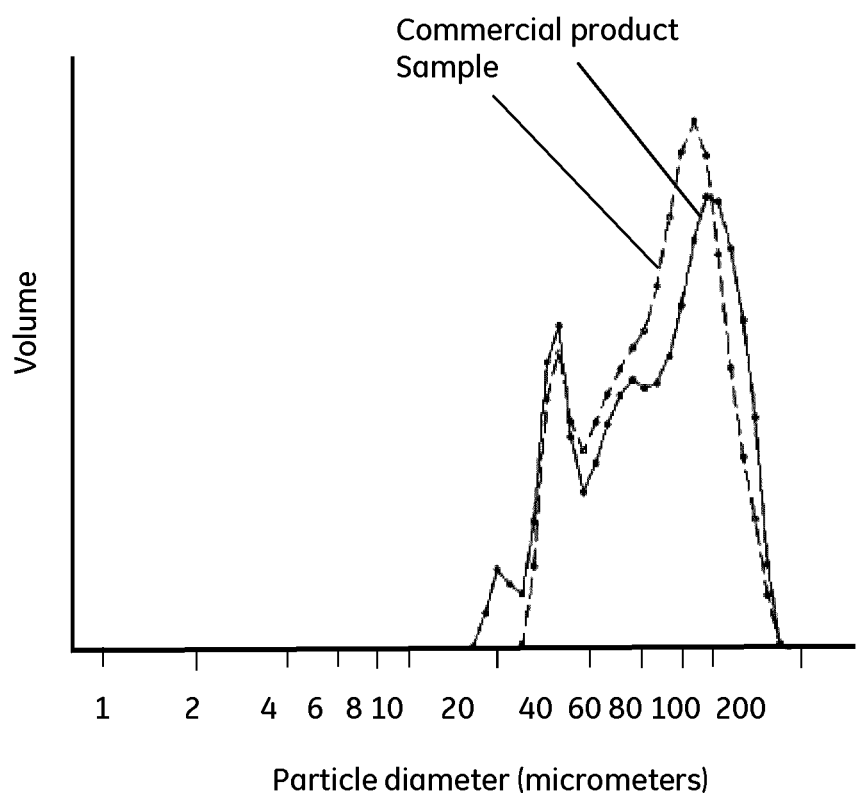
FIG. 5 illustrates particle size distribution curves of the agarose bead sample and a commercial agarose bead product, respectively.

Experiments were carried out to investigate particle size distribution of the agarose beads. A Beckman Coulter particle analyzer was used to measure particle size distributions of the agarose beads obtained in this example (Sample) and commercial agarose beads produced with emulsion processes (Commercial Product), respectively. The detailed size distribution data is shown in the Table 1 below. The particle size distribution curves are illustrated in FIG. 5.

TABLE 1

Detailed size distribution data

| Beads | Beads size distribution (μm) | | | |
|---|---|---|---|---|
| | Mean diameter | Median/d50 | d10 | d90 |
| Sample | 72.46 | 71.16 | 32.46 | 114.3 |
| Commercial Product | 74.05 | 71.69 | 29.33 | 124.5 |

The d values such as d10, d50 and d90 in the Table 1 and FIG. 5 are important parameters of describing particle size distributions. d10 is the value of the particle diameter at 10% in the cumulative distribution. d50 is the value of the particle diameter at 50% in the cumulative distribution, and it is also known as the median diameter or the medium value of the particle size distribution. d90 is the value of the particle diameter at 90% in the cumulative distribution. For example, if d10=32.46 μm, then 10% by volume of the particles in the sample are smaller than 32.46 μm, and if d90=114.3 μm, then 90% by volume of the particles in the sample are smaller than 114.3 μm.

It can be seen that the agarose beads obtained in this example have a good particle size distribution, which is better than that of the commercial agarose beads produced with emulsion processes.

Experiments also were carried out to investigate the separation performance of the agarose beads obtained in this example. A liquid chromatographic analyzer (AKTA Avant 150, from General Electric Company) was used to analyze separation performances of the Sample and the Commercial Product, respectively. The analyses were carried out under the following conditions:
Buffer: 0.05M phosphate, 0.15M sodium chloride (NaCl), pH=7.2;
Equilibrate: 2 Column Volume (CV);
Elution: 3 CV;
Flow rate: 0.3 mL/min;
Sample or Commercial Product volume: 100 μL (injected by 200 μL Sample Loop).

Figure 6:
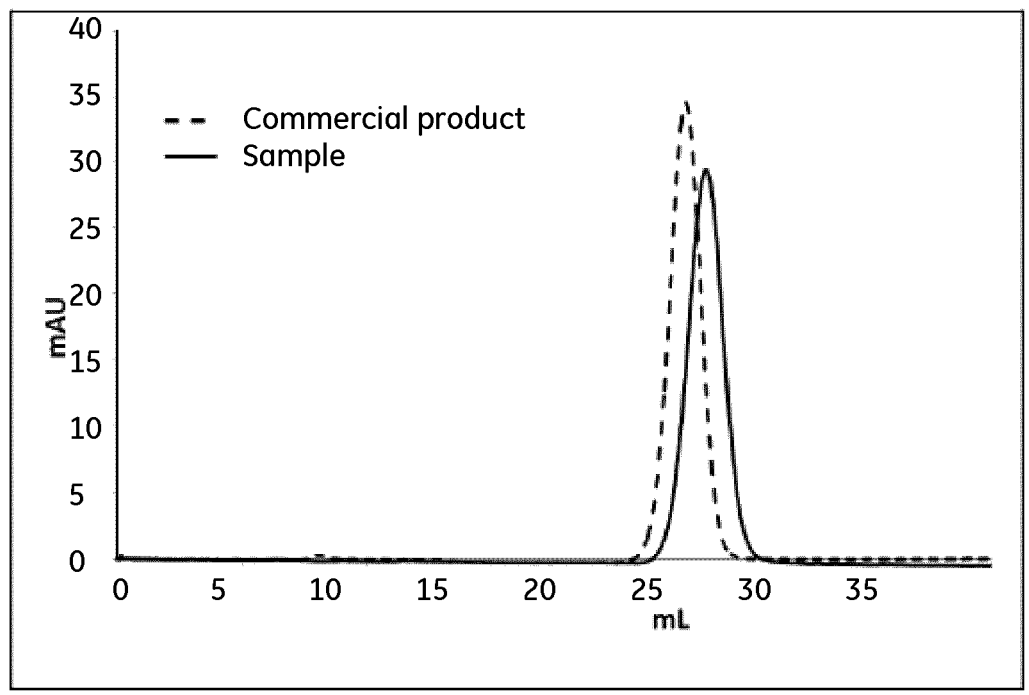
FIG. 6 illustrates column performance evaluation curves of the agarose bead sample and the commercial agarose bead product, respectively.

The measured data evaluating the separation performances is shown in the Table 2 below. The column performance evaluation curves are illustrated in FIG. 6. N, the number of theoretical plates, is an index used to determine the liquid chromatography column efficiency. Columns with high plate numbers are considered to be more efficient (i.e., higher column efficiency) than columns with lower plate numbers. $V_0$ is the column void volume. Kay indicates a ratio between the elution volume of a given molecule and the total available volume of the column, and is defined as $(V_e-V_0)/(V_t-V_0)$ where $V_e$ is the elution volume, $V_0$ is the void volume and $V_t$ is the total column volume. It always has a value between 0 and 1.

TABLE 2

Data evaluating the separation performances

| Beads | Separation Performances | | |
|---|---|---|---|
| | N per meter | $V_0$ (mL) | Kav |
| Sample | 4698.5 | 6.628 | 0.737 |
| Commercial Product | 5223.8 | 8.333 | 0.807 |

It can be seen that the agarose beads obtained in this example have a similar separation performance versus the commercial agarose beads produced with emulsion processes when stacked in volume for size exclusion-based separation.

In one example, the air interval distance D was varied between 35 and 100 cm, for a nozzle with spray angle 13 degrees. As shown in Table 3, the particle size distributions were narrower for the higher values of D. The shape of the beads was also more spherical at higher D values and less aggregation of the beads was observed.

TABLE 3

Effect of the orifice-collecting surface distance D on the particle size distribution.

| D (cm) | Mean diameter (micrometers) | Median diameter (micrometers) | Standard deviation (micrometers) | d10 (micrometers) | d90 (micrometers) |
|---|---|---|---|---|---|
| 35 | 85.1 | 63.1 | 73.2 | 26.9 | 168 |
| 70 | 78.6 | 65.2 | 55.7 | 28.9 | 142 |
| 100 | 76.3 | 67.8 | 41.9 | 29.7 | 136 |

The invention may be embodied in other specific forms without departing from the spirit or essential characteristics thereof. The foregoing embodiments are therefore to be considered in all respects as illustrative rather than limiting on the invention described herein. The scope of embodiments of the invention is thus indicated by the appended claims rather than by the foregoing description, and all changes that come within the meaning and range of equivalency of the claims are therefore intended to be embraced therein.

The invention claimed is:

1. A method, comprising:
    spraying a liquid comprising a polysaccharide, and a gas, substantially inert to the liquid, respectively from a first and a second orifice of a nozzle into air to form a mist of beads, wherein the nozzle is a two-phase spray nozzle configured to atomize the liquid by causing interaction of the liquid and gas from the first and second orifices respectively; and
    collecting the beads with a collecting medium at a temperature in a range from about −10° C. to about 80° C., the collecting medium comprising water, alcohol, or a combination thereof.

2. The method according to claim 1, wherein the liquid is an aqueous solution of the polymer.

3. The method according to claim 1, wherein the polysaccharide comprises agarose, dextran, cellulose, or combinations thereof.

4. The method of claim 1, wherein the polysaccharide comprises native or derivatised agarose or agar.

5. The method according to claim 1, wherein the collecting medium is water or an aqueous solution comprising at least 80 or 90 wt. % water.

6. The method according to claim 1, further comprising feeding the liquid into the nozzle at a temperature in a range from about 65° C. to about 100° C.

7. The method according to claim 1, wherein the nozzle is configured to produce a substantially conical spray pattern with a spray angle of less than 90 degrees.

8. The method according to claim 1, wherein the liquid and gas are fed into the nozzle under different conditions comprising pressures, temperatures, flow rates, or combinations thereof.

9. The method according to claim 1, wherein a mass flow rate ratio between the liquid and the gas is in a range from about 0.1 to about 10.

10. The method according to claim 1, wherein the distance between the first and second orifice and a surface of the collecting medium is at least 25 cm.

11. The method according to claim 1, further comprising dispersing the collecting medium.

12. The method according to claim 1, wherein a relative humidity in an air interval between the first and second orifice and a surface of the collecting medium is controlled to be at least 90%.

13. The method according to claim 1, further comprising cooling the mist of beads to obtain solid microparticles of the polymer, wherein the microparticles have a diameter in a range from about 20 micrometers to about 500 micrometers.

14. The method according to claim 1, further comprising cooling the mist of beads to obtain solid microparticles of the polymer, wherein the microparticles have a volume-weighted median diameter in a range from about 30 micrometers to about 100 micrometers.

15. The method of claim 12, further comprising a step of crosslinking said microparticles.

16. The method of claim 12, further comprising a step of derivatizing said microparticles with ligands.

17. The method of claim 12, further comprising a step of using said microparticles in chromatographic separation of a target molecule.

18. A system, comprising:

- a nozzle configured to spray a liquid comprising a polysaccharide and a gas substantially inert to the liquid from a first and second orifice thereof, respectively, to form a mist of beads, wherein the nozzle is a two-phase spray nozzle which atomizes the liquid by causing interaction of the gas and liquid from the first and second orifices respectively;
- a liquid feeding device configured to feed the liquid into the first orifice of the nozzle;
- a gas feeding device configured to feed the gas to the second orifice of the nozzle; and
- a receiving unit containing a collecting medium for collecting the beads, the collecting medium comprising at least one of water and alcohols.

19. The system according to claim 18, wherein the first and second orifices are spaced apart from a collecting surface of the collecting medium in the receiving unit.

20. The system according to claim 19, wherein the first and second orifices are no less than about 5 centimeters from the collecting surface.

21. The system according to claim 18, further comprising a control device configured to adjust a mass flow rate ratio between the liquid and the gas.

22. The system according to claim 18, further comprising a control device configured to enable the liquid and gas to be fed into the nozzle under different conditions comprising pressures, temperatures, flow rates, or combinations thereof.

23. The system according to claim 18, further comprising at least one of a heating device and a thermo-insulation device thermally coupled to the liquid feeding device.

24. The system according to claim 18, further comprising at least one of a heating device and a thermo-insulation device thermally coupled to the nozzle.

25. The system according to claim 18, wherein the second orifice comprises an annular opening surrounding the first orifice.

26. The system according to claim 18, further comprising a dispersing device configured to disperse the collecting medium.

27. The system according to claim 18, wherein the nozzle is configured to produce a conical spray pattern with a spray angle of less than 90 degrees or less than 45 degrees.

28. The system according to claim 18, wherein the distance between the first and second orifice and a surface of the collecting medium is at least 25 cm, or at least 70 cm.

29. The system according to claim 18, wherein the collecting medium is water or an aqueous solution comprising at least 80 or 90 wt. % water.

30. The system according to claim 18, further comprising a control device configured to control a relative humidity in an air interval between the first and second orifice and a surface of the collecting medium to be at least 90%.

* * * * *